United States Patent [19]

Tomoff et al.

[11] 4,294,126

[45] Oct. 13, 1981

[54] SAMPLE FEEDING DEVICE

[75] Inventors: Toma Tomoff; Wolfgang Chlosta, both of Überlingen; Heinz Henninger, Owingen; Rolf Tamm, Salem; Klaus Grossmann, Owingen, all of Fed. Rep. of Germany

[73] Assignee: Bodenseewerk Perkin-Elmer & Co., GmbH, Fed. Rep. of Germany

[21] Appl. No.: 102,704

[22] Filed: Dec. 12, 1979

[30] Foreign Application Priority Data

Jan. 2, 1979 [DE] Fed. Rep. of Germany ....... 2900066

[51] Int. Cl.³ .................... G01N 35/04; G01N 35/06
[52] U.S. Cl. ............................. 73/864.21; 73/864.25; 422/64
[58] Field of Search .................. 73/423 A; 422/64; 222/136; 250/566

[56] References Cited

U.S. PATENT DOCUMENTS

| | | | |
|---|---|---|---|
| 3,328,591 | 6/1967 | Jones | 250/566 |
| 3,636,777 | 1/1972 | Frank | 422/64 |
| 3,841,160 | 10/1974 | Iwao | 73/422 GC |
| 4,068,529 | 1/1978 | Konig | 73/423 A |
| 4,111,051 | 9/1978 | Tamm | 73/423 A |

Primary Examiner—S. Clement Swisher
Attorney, Agent, or Firm—S. A. Giarratana; F. L. Masselle; R. A. Hays

[57] ABSTRACT

A sample feeding device includes a turntable driven by a servomotor and mounted on a carrier driven by a separate servomotor. The turntable servomotor and the carrier servomotor, as well as a movable intake tube, are controlled by a control device.

9 Claims, 10 Drawing Figures

SAMPLE FEEDING DEVICE

The invention relates to a sample feeding device for automatically feeding samples into a graphite tube atomizer provided with a sample inlet opening, comprising: a turntable adapted to accomodate a circular array of liquid vessels, a turntable servomotor for driving the turntable, an intake tube movable between a first position and a second position by means of an intake tube servomotor, said intake tube, in its first position, dipping with one end into a respective liquid vessel located in an operative position, and, in its second position, extending with this one end into the sample inlet opening of the graphite tube atomizer, a sample pump, which is connected to the other end of the intake tube and adapted to suck in liquids and to discharge them again through the intake tube, and a control device, which is adapted to control the intake tube servomotor, the turntable servomotor and the sample pump in accordance with a certain program such that consecutively liquids from different liquid vessels are sucked into the intake tube and are discharged into the graphite tube atomizer.

A sample feeding device for automatically feeding samples into a graphite tube atomizer provided with a sample inlet opening is known from the German patent application laid open No. 25 07 260. The prior art sample feeding device comprises a turntable, which is adapted to accommodate a circular array of liquid vessels which contain the samples to be supplied. A turntable servomotor serves to drive the turntable. In the prior art device this is done in the following manner: The turntable is arranged on a carrier, which is rotatable between two stops about an axis which is located outside the axis of rotation of the turntable. In one position of the carrier, a liquid vessel of the turntable is in an operation position. In the other position of the carrier a rinsing vessel, which if fixedly mounted on the carrier, is in the operative position. The turntable servomotor rotates the carrier, which is a sector-shaped plate, between two stops. By means of a ratchet mechanism with pawls and ratchet teeth provided along the circumference of the turntable, the turntable is advanced by one step during each of these rotating movements, such that the next liquid vessel of the circular array will then be located in the operative position. An intake tube with square-off end is movable between a first and a second position by means of an intake tube servomotor. In its first position, the intake tube with its squared-off end dips into the respective liquid vessel located in the operative position. In its second position, it extends with this square-off end into the sample inlet opening of the graphite tube atomizer. This is made possible by the intake tube carrying out a totation through 180° about its longitudinal axis simultaneously with its swinging movement from its first to its second position, whereby the squared-off end extends downwardly in both positions. A sample pump and a rinsing liquid pump is connected to the other end of the intake tube. The sample pump is adapted to suck liquid quantities in and to discharge them again through the intake tube, while the rinsing liquid pump due to check valves feeds in one direction only and can discharge rinsing liquid from a rinsing liquid container through the intake tube.

The intake tube dips into a liquid vessel on the turntable. The sample pump sucks a well-defined volume of sample liquid in. Then the intake tube is swung into its second position and dispenses the sample liquid into the graphite tube. The carrier is rotated such that now the rinsing vessel is in the operative position. The intake tube is swung back into its first position and dips into the rinsing vessel. The rinsing liquid pump presses rinsing liquid through the intake tube into the rinsing vessel, which is designed as an overflow vessel, whereby the intake tube is cleaned from remnants of the sample just dispensed. Thereafter the intake tube is moved out of the rinsing vessel. The carrier is rotated back by the turntable servomotor, whereby the turntable is advanced by one step, through the ratchet mechanism. Now the next liquid vessel of the turntable is in the operative position. The intake tube is now able to dip into this vessel, in order to feed the next sample to the graphite tube.

Furthermore it is known from German patent specification laid open No. 26 02 675 to supply a sample to be tested from a liquid vessel on the turntable to a graphite tube by means of an intake tube and a sample pump in a first measuring cycle, and subsequently, in a second measuring cycle to supply this sample and in addition, a metered quantity of an addition liquid to the graphite tube. To this end, an additional liquid vessel with an addition liquid is arranged on the carrier, which is in the form of a sector-shaped plate. The carrier is rotatable between a fixed stop and a stop, which is movable between two positions. With the carrier in engagement with the fixed stop, a liquid vessel of the turntable is in the operative position. When the carrier engages the movable stop, the additional liquid vessel is in the operative position in one position of this stop and the rinsing vessel is in the operative position in the other position of this stop. The movable stop is controlled mechanically by a servomotor, this servomotor as well as the turntable servomotor, which in this case rotates the carrier, the intake tube servomotor and the sample and rinsing liquid pumps being controlled by a control device. Also in this prior art arrangement the turntable is advanced by one step during the swinging movement of the carrier by means of a ratchet mechanism. Furthermore from German patent specification laid open No. 26 16 501, an apparatus for automatically feeding samples to an analytical instrument is known, wherein a single driving motor, through an appropriate ratchet mechanism, both rotates the intake tube and effects the rotary movement of the carrier, by which movement, in turn the turntable is advanced.

From German patent specification laid open No. 26 04 170, eventually, a device for automatically feeding liquid samples to an analytical instrument is known, wherein an additional turntable is arranged on the carrier side-by-side with the turntable containing the samples, said additional turntable containing neutral or calibrating solutions. By rotary movement of the carrier a liquid vessel of this second turntable can be moved into the operative position below the intake tube, whereby consecutively different calibration solutions or the neutral solution are supplied to the graphite tube by advancing this second turntable. Such an arrangement permits calibration or re-calibration of the instrument in accordance with a desired program, permitting also non-linearities of the calibration characteristic to be taken into account by using different calibration solutions.

In the prior art sample feeding devices the liquid vessels are arranged on the turntable in a single circular array, and one after the other of these liquid vessels is moved into the operative position in fixed sequence.

The program is determined by mechanical means and is therefore not very flexible.

It is the object of the invention to construct a sample feeding device of the type defined in the beginning such that the movements of the turntable can be selected freely by control signals which are provided by the control device, whereby greater flexibility of the program can be achieved and the sample feeding device can more easily adapted to the various problems.

According to the invention this object is achieved in that a turntable position sensor is connected to the turntable and supplies a turntable position signal to the control device, and that the turntable is arranged to be rotated by the turntable servomotor into positions determined by the program of the control device only and monitored by the turntable position signal.

Thus the turntable provides turntable position signals by means of the turntable position sensor, said signals identifying the various positions of the turntable in which a respective one of the liquid vessels is in the operative position. Then the liquid vessels can be moved into the operative position in optional sequence depending on the control program. At the same time, the turntable position signals permit the respective measuring data to be associated with a particular sample vessel.

For example some liquid vessels on the turntable may then be filled with blank or calibration solution. Then the turntable, after a predetermined number of measurements, can move these liquid vessels into the operative position to initiate re-calibration. This is determined only by the program of the control device and not by the sequence of vessels on the turntable.

Therefore it is neither necessary to provide vessels with blank and calibration solutions again and again in certain intervals along the turntable, which would reduce the number of measuring samples accommodated by the turntable, nor is a separate second turntable required, which has to be moved into the operative position by mechanical means.

Further modifications of the invention are subject matter of the sub-claims.

An embodiment of the invention is described in greater detail hereinbelow with reference to the accompanying drawings.

Figure 1:
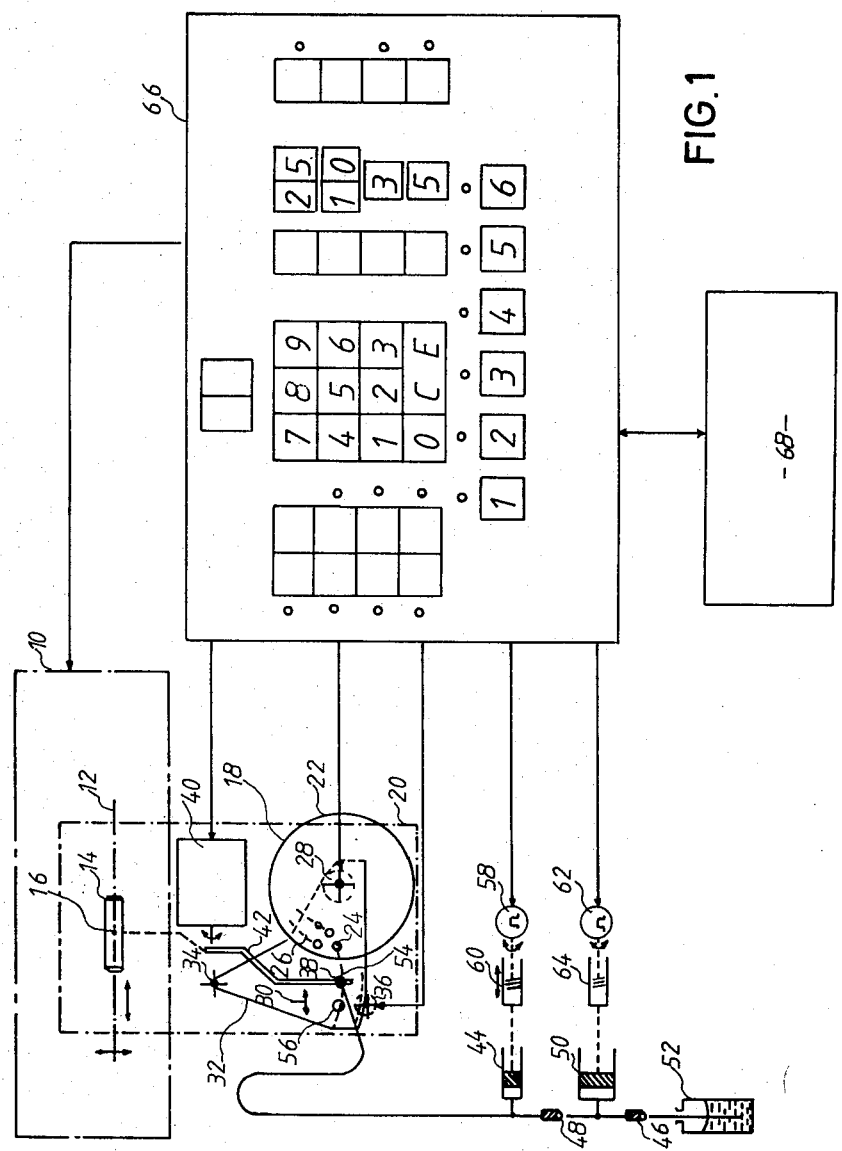
FIG. 1 shows schematically a block diagram of a sample feeding device with the graphite tube atomizer, the atomic absorption spectrometer and the control devices for sample feeding device and graphite tube atomizer.

The block diagram of FIG. 1 shows the construction of a measuring station for automatically carrying out consecutive measurements by means of flameless atomic absorption spectroscopy.

Numeral 10 designates an atomic absorption spectrometer the measuring beam 12 of which passes through a graphite tube atomizer, which is indicated by the graphite tube 14. The graphite tube 14 has a sample inlet opening 16. A sample feeding device is generally designated by numeral 18. The sample feeding device 18 is mounted, together with the graphite tube atomizer, on a common, stationary base plate 20.

The sample feeding device 18 comprises a turntable 22 which accommodates liquid vessels in two concentric circular arrays 24,26. The turntable is arranged to be driven by a turntable servomotor 28. The turntable 22 with the turntable servomotor is arranged on a carrier 32, which is tranversely movable relative to the instrument base plate 20 in the direction of the arrow 30. The carrier has the form of a sector-shaped plate, which is rotatable about a pivot axis 34 spaced from the axis of the turntable 22. The carrier 32 is arranged to be rotated by means of a separate carrier servomotor 36. Thus contrary to the prior art sample feeding devices separate servomotors are provided for the turntable and for the carrier.

An intake tube 38 is movable between a first and a second position by means of an intake tube servomotor 40 through a swinging lever. In its first position illustrated in solid lines the intake tube with one end dips into a respective liquid vessel located in the operative position. In its second position illustrated in dashed lines, the intake tube 38 extends with this one end into the sample inlet opening 16 of the graphite tube atomizer. A sample pump 44 is connected to the other end of the intake tube 38 and is adapted to suck in liquid quantities in and to dispense them again through the intake tube. Furthermore a rinsing liquid pump 50 feeding in one direction only and provided with check valves 46,48 is connected to said other end of the intake tube 38 and communicates with a rinsing liquid container 52.

A waste vessel 54 as well as a further liquid vessel 56 fixedly arranged on the carrier 32 are placed on the carrier radially outside of the turntable 22.

The sample pump 44 is arranged to be actuated by a stepping motor 58 through a spindle drive 60. The rinsing liquid pump 50 is arranged to be actuated by a stepping motor 62 through a spindle drive 64.

A control device 66 controls, in accordance with a predetermined program, the carrier servomotor 36, the turntable servomotor 28, the stepping motors 58 and 62 for the sample and flushing liquid pumps 44 and 50, respectively, the intake tube servomotor 40 as well as the heating of the graphite tube 14, the duration and temperature of said heating being determined by the power unit 68. The power unit 68 may be constructed as shown in German patent No. 2 008 295.

Figure 2:
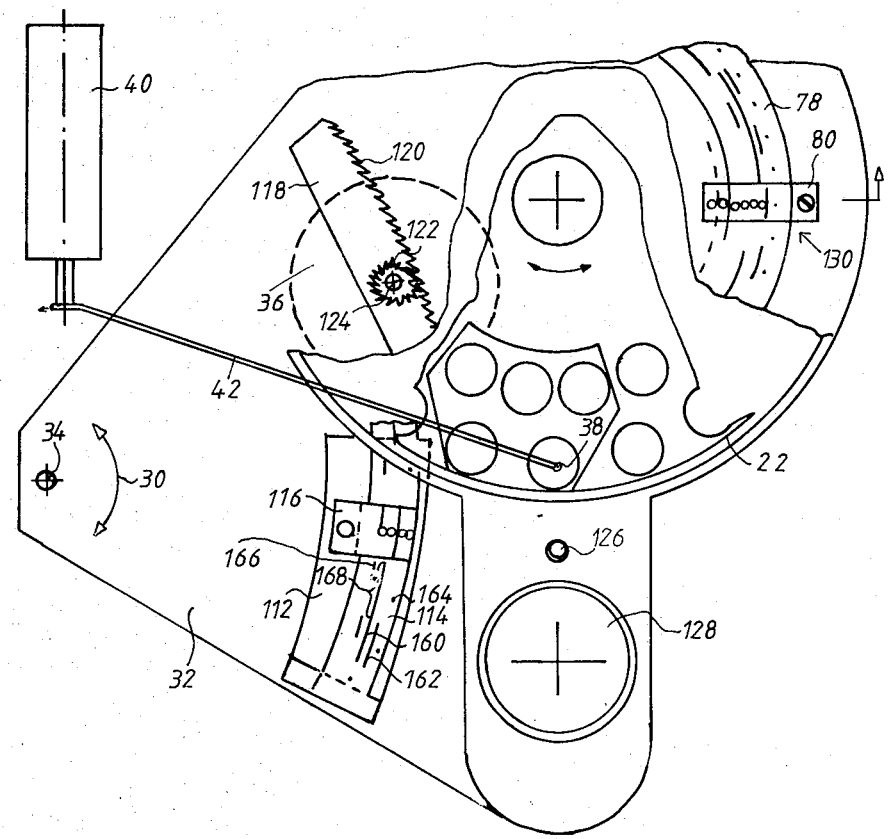
FIG. 2 is a fractional plan view of a sample feeding device according to the invention.
Figure 3:
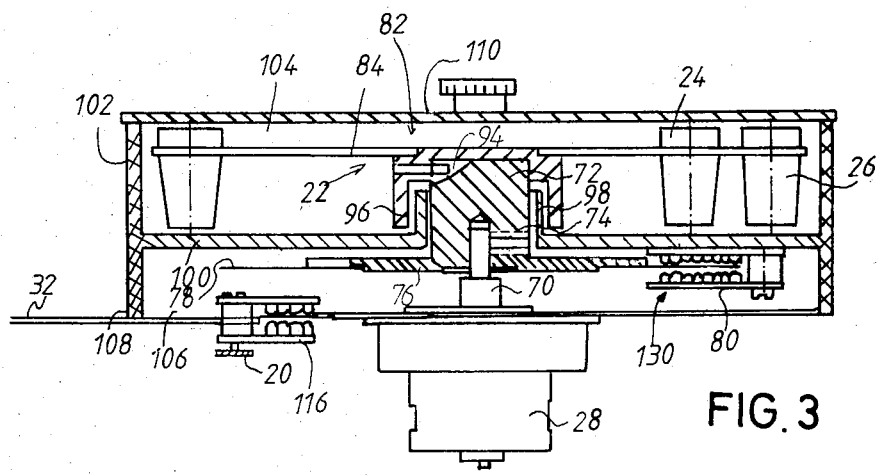
FIG. 3 is a sectional view taken along line A-A of FIG. 2.
Figure 5:
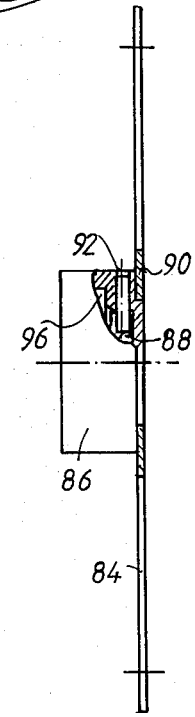
FIG. 5 is a vertical sectional view of the sample tray.

The construction of the sample feeding device is illustrated in detail in FIGS. 2 and 3. The turntable servomotor 28 is mounted below the carrier 32, as illustrated in FIG. 3, and extends with its shaft 70 upwardly and through the carrier. A hub 72 is placed on the shaft 70 of the turntable servomotor 28 and is non-rotatably attached to the shaft 70 by means of a screw 74. The hub 72 carries a code disc 78 at its disc-shaped end 76. The code disc coacts with a light barrier assembly 80 in a manner still to be described. A sample tray 82 is placed centrally on the hub 72. Such a sample tray is illustrated in FIG. 5 in a vertical sectional view. The sample tray 82 comprises a plane tray portion 84 and a central sleeve 86 with a stepping bore, the inner portion 88 of which of smaller diameter is pushed fittingly on the hub 72, whereby the sample tray 82 is centered on the hub 72. A pin 90 is located in a radial bore 92 of the sleeve 86 and extends into a recess 94 of the hub, when the sample tray is in its correct angular position with respect to the hub 72 and thus to the code disc 78. An enlarged portion 96 of the stepped bore accomodates a collar 98 of a partition 100, said collar extending between the sleeve 86 and the hub 72. The partition 100 forms part of a housing 102 and separates the housing chamber 104, in which the sample tray 82 with the sample vessels 24,26 is located, from the housing chamber 106, which is defined between the partition 100 and the carrier 32 and which contains the code disc 78 and the light barrier assembly 80. The housing 102 engages the carrier 32 by means of a seal 108. The housing 102 is closed on the top by means of a cover 110, which has apertures only in the area of the operative positions of the liquid vessels 24,26, the intake tube being adapted to pass through said apertures.

As can be seen from FIGS. 2 and 3, the carrier 32 has an aperture 112 therethrough, across which a transparent code disc 114 extends, which is of arcuate shape and is curved about the pivot axis 34. The code disc 114 is scanned by a light barrier assembly 116, which is attached to the base plate 20.

Furthermore the carrier 32 has an aperture 118 therethrough, which on one side forms a gearing 120. A pinion 122 meshes with this gearing 120 and is attached to the shaft 124 of the carrier servomotor 36.

A rinsing vessel 126 and an additional liquid vessel 128 are mounted on the carrier 32 radially outside the turntable. The arrangement is such that with rotary movement of the carrier 32 into four different positions thereof a vessel 24 of the inner circular array, a vessel 26 of the outer circular array, the rinsing vessel 126 or the additional liquid vessel 128 get into the operative position below the intake tube 38.

Figure 7:
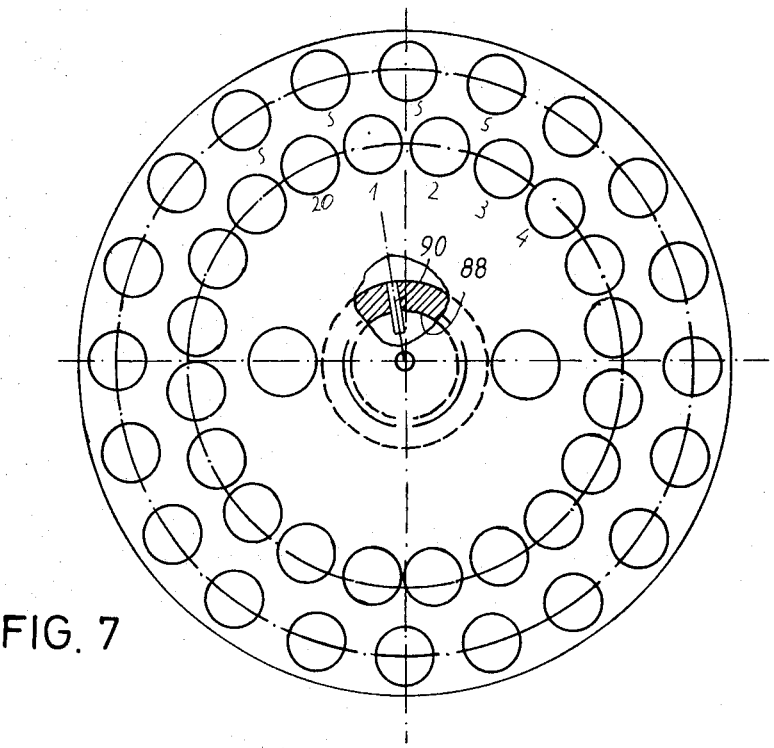
FIG. 7 shows a turntable for the automatic carrying out of the addition method.
Figure 4:
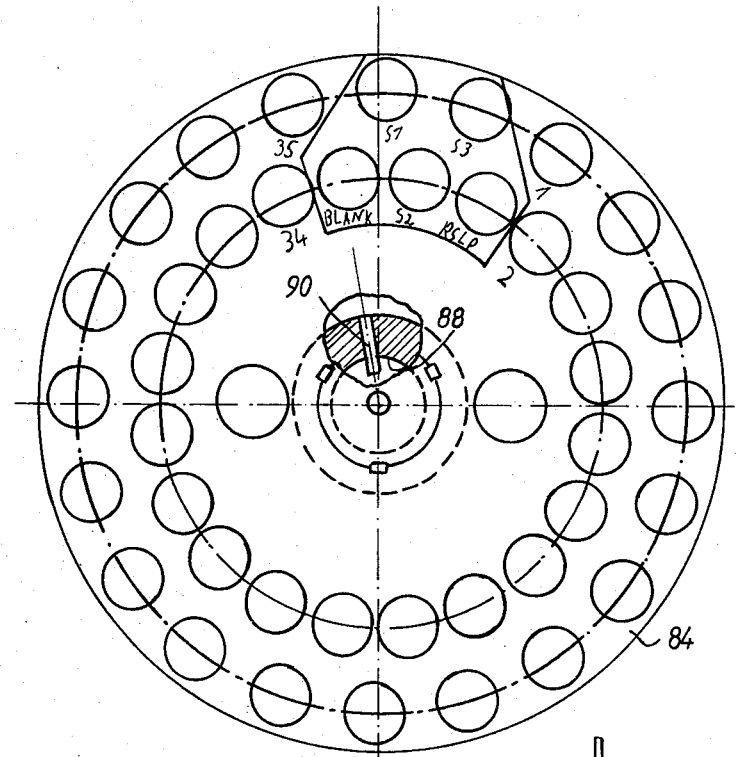
FIG. 4 is a plan view of the sample tray of a turntable, which is adapted to the conventional mode of feeding samples.
Figure 6:
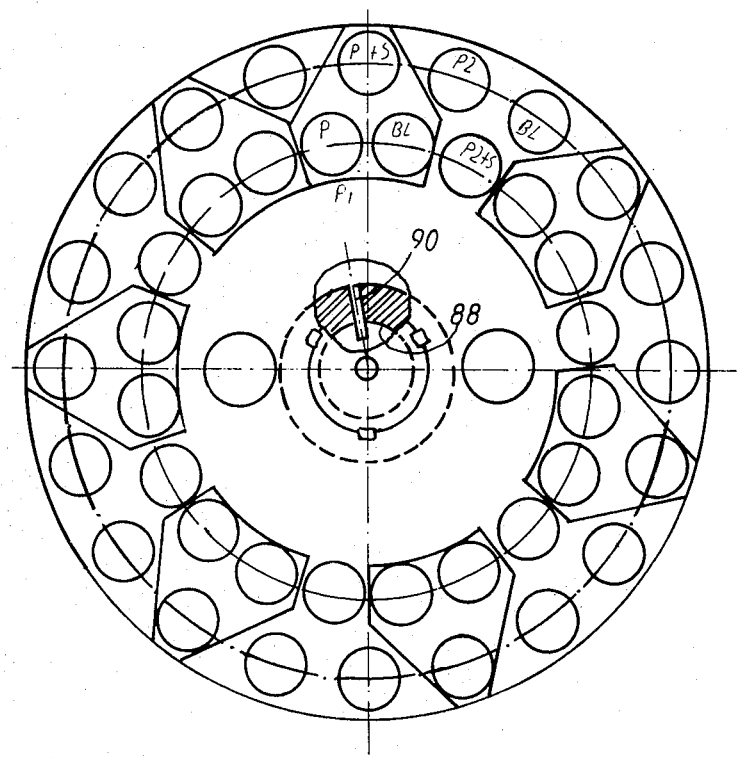
FIG. 6 is a plan view of a sample tray for the addition method.
Figure 9:
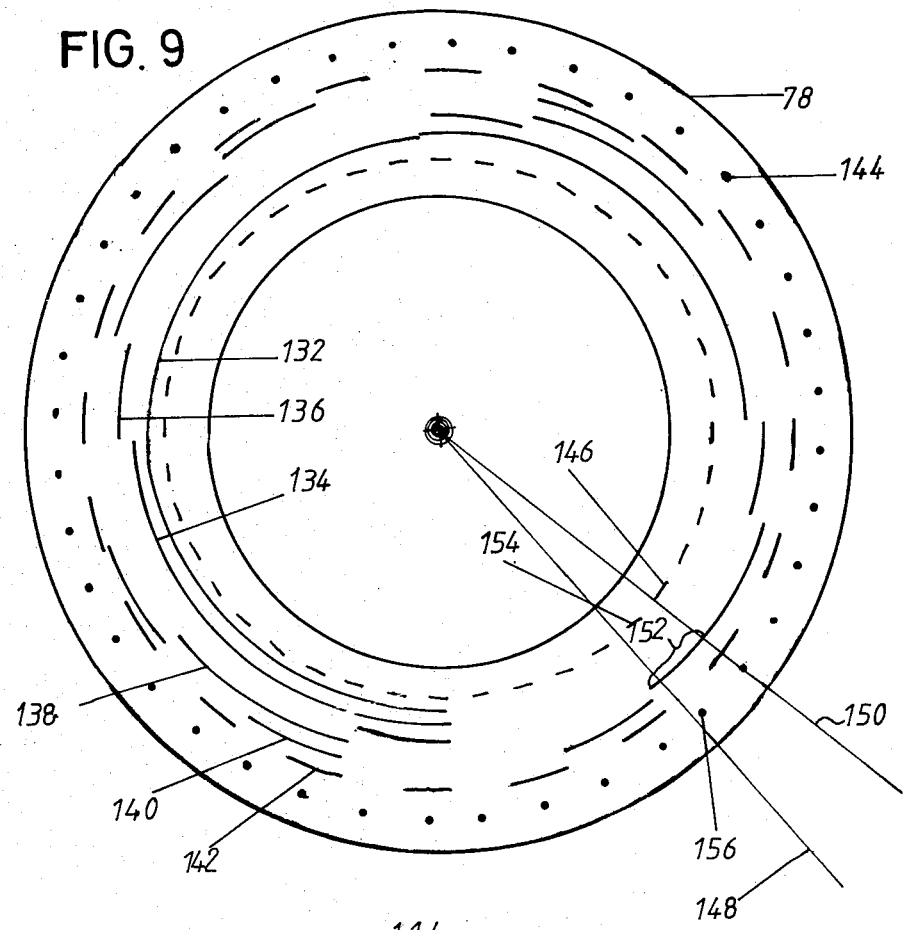
FIG. 9 shows the code disc serving as turntable position sensor.
Figure 8:
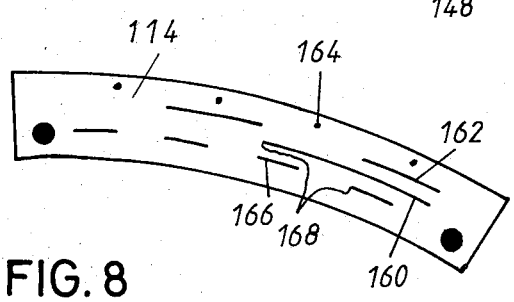
FIG. 8 shows the code disc serving as carrier position sensor.

After the cover 110 has been removed, the sample tray 82 can be removed with the pin 90 guided in a slot of the hub 72 and can be replaced by another sample tray. The various sample trays as illustrated in FIGS. 4, 6 and 7 have identical arrangements of apertures for accommodating sample vessels but are marked in different manners, in order to facilitate the placement of the sample vessels for the carrying out of the various programs.

The code disc 78 and the light barrier assembly 80 form a turntable position sensor 130 which provides a turntable position signal in accordance with the position of the turntable. The turntable code disc 78 is an annular disc of transparent material which comprises six circular tracks 132,134,136,138,140, and 142 with opaque markings, which are scanned by light barriers of the light barrier assembly 80, the various angular positions of the turntable 18 being encoded digitally by the markings. In order to mark the positions exactly, to which the turntable is rotated, a further track 144 of the turntable code disc 78 is provided with dotted marks, each of which marks one of the encoded positions of the turntable 18 in which a liquid vessel 24,26 is in the operative position below the intake tube. A further track 146 of the turntable code disc 78, which track is arranged to be scanned by a light barrier, has dashed or arcuate marks, which extend from the radius 148 passing through a respective one of the dotted marks to the radius 150 which passes through the end of the marking 152 encoding the respective position of the turntable 18. When the position marking 152 selected by the program has been reached, the direction of rotation of the turntable servomotor 28 is arranged to be controlled depending on such an arcuate mark 154 being detected or not such that the associated dotted mark 156 is set on the light barrier responding thereto.

The carrier position sensor 158 comprises the carrier code disc 114 connected to the carrier, and the light barrier assembly 116. The carrier code disc consists of transparent material and has two tracks 160,162 with opaque markings, which are arranged to be scanned by light barriers. The various positions of the carrier 32 are encoded digitally by these markings, whereby four different positions can be selected. In the first position the intake tube 38 is located above the inner circular array 24 of liquid vessels of the turntable 18, in the second position it is located above the outer circular array of liquid vessels of the turntable 18, in the third position it is located above the rinsing vessel 126 and in the fourth position it is located above the additional liquid vessel 128. A further track 164 of the carrier code disc arranged to be scanned by a light barrier has dotted marks, each of which marks corresponding to an exactly defined position of the carrier 32, which position is designated by the code. A further track 166 of the carrier code disc 114 arranged to be scanned by a light barrier has dashed or arcuate marks therein, each of which extends from a spot on the track adjacent a respective one of the dotted marks to the spot, which is adjacent the end of the marking 168 encoding the position of the carrier 32 associated with this dotted mark. When the position marking 168 selected by the program has been reached, the direction of rotation of the carrier servomotor 36 is arranged to be controlled depending on such an arcuate mark being detected or not, such that the associated dotted mark is set on the light barrier responding thereto.

Thus the dashed or arcuate marks in the tracks 146 of the turntable code disc 78 and 166 of the carrier code disc 32 determine the direction of rotation of the servomotors, by means of which the turntable and the carrier, respectively, is accurately positioned.

Figure 10:
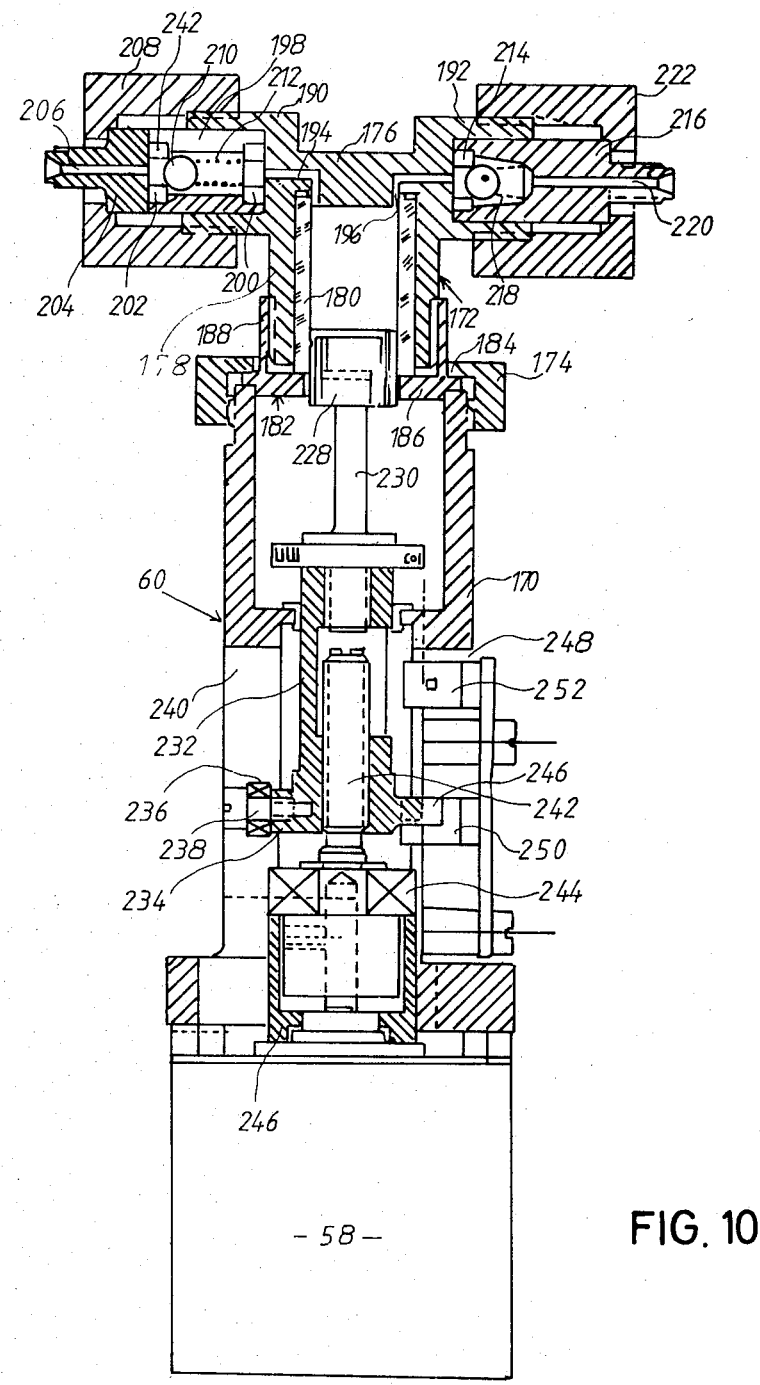
FIG. 10 is a longitudinal sectional view of the rinsing liquid pump.

FIG. 10 illustrates a longitudinal sectional view of the sample pump and the associated drive means.

The stepping motor 58 is secured to a housing 170. A pump cylinder assembly 172 is screwed to the upper end of the housing 170 by means of a cap nut 174. The pump cylinder assembly contains a tee 176 with a socket 178, which accommodates the pump cylinder 180 formed by a glass sleeve. The pump cylinder 180 is located between the tee 176 at the bottom of the socket 178 and a bushing 182, which with a radial flange engages the end face of the cylindrical housing 170 and is screwed thereto by means of the cap nut 174, and which forms an annular disc 186 extending inwardly and a collar 188. The pump cylinder engages the annular disc 186 with its end face. The socket 178 is screwed into the collar 188, whereby the pump cylinder is firmly retained. The tee 176 forms two opposite pot-shaped projections 190 and 192. A bushing 198 is located within the pot-shaped projection 190. A ring 200 is retained between a shoulder of the bushing 198 and the bottom of the pot-shaped recess 190. A second ring 202 is located at the other end in the bushing 198 and engages a shoulder thereof. An inlet piece 204 contains a central passage 206 and engages the ring 202 with its end face. The inlet piece is held by a cap nut 208, which is screwed on the pot-shaped projection 190. A valve ball 210 engages the ring 202 under the action of a coil spring, said ring thus acting as a valve seat. The coil spring 212 is supported by the ring 200. This assembly functions as a check valve, which permits liquid to flow through the passage 206, through the bore of the ring 202, the interior of the bushing 198 and the bore of the ring 200 to the passage 194 and into the cylinder 180, but which shuts off any flow in opposite direction.

In similar manner a check valve is provided in the pot-shaped projection 192 and permits flow from the cylinder 180 through the passage 196. The check valve comprises a ring 214 acting as a valve seat and being retained between the bottom of the pot-shaped projection 192 and a shoulder of an outlet body 216. The outlet body 216 has a recess 218 and an outlet passage 220. It is retained in the pot-shaped projection 192 by means of a cap nut 222. A valve ball 224 is located within the recess 218 and engages the ring 214 acting as a valve seat under the action of a spring 226. The spring 226 abuts the bottom of the recess 218 around the outlet passage 220.

A piston 228 is guided in the cylinder 180. A piston rod 230 is connected to a sleeve-shaped nut 232. The nut 232 has a radial projection 234. A ball bearing 236 is clamped with its inner race to the projection by means of a screw 238. With its outer race, the ball bearing is guided in a longitudinal slot 240 of the housing 170. Thereby the nut 232 is prevented from rotation.

The nut 232 is arranged on a spindle 242. The spindle is rotatably mounted in the housing 170 by means of a ball bearing 244 and a bushing 246 but is secured against axial movements. It is driven by the stepping motor 58.

When the stepping motor 58 and the spindle 242 make a rotary movement, the nut 232, which is secured against rotation, will be moved axially. Thereby also the piston 228 is moved in the cylinder 180. The piston stroke depends on the number of the pulses which are applied to the stepping motor.

A lug 246 is attached to the nut 232 and is movable in a slot 248 of the housing 170. The lug covers light barriers 250 and 252 in each of the two end positions of the piston 228. The energization of the stepping motor is interrupted by these light barriers, when the piston has reached one of its end positions.

When the apparatus is switched on, the control device 66 energizes the stepping motor 58 at first to move into the reference position defined by said one light barrier 250, the steps which determine the position of the pump piston 228 being then counted from this reference position. Thus the light barrier 250 represents a sensor which responds to a well defined reference position of the spindle drive and of the pump piston 228.

The rinsing pump is of similar construction as the sample liquid pump illustrated in FIG. 10. However there are no check valves.

The arrangement described operates as follows:

After the apparatus has been switched on by pushing a key START, the rinsing liquid pump supplies a fixed quantity, for example 1.2 milliliters, of rinsing liquid through the intake tube into the rinsing vessel 54, which is designed as an overflow vessel. Thereby the intake tube is cleaned on the inside and on the outside from the previous sample. Thereafter the lever 42 lifts the intake tube 38 out of the rinsing vessel. The sample pump sucks in a fixedly set quantity (30 microliters) of air. The carrier is rotated laterally, and the intake tube dips into the first liquid vessel of the turntable 18 containing sample. The sample pump sucks in a selected quantity, for example 25 microliters, of sample liquid. At the same time, the rinsing liquid pump 50 sucks in new rinsing liquid. Thereafter the arm 42 rotates the intake tube 38 into the graphite tube 14, and the sample pump 44 dispenses the 25 microliters of sample liquid and 15 microliters of air. Then the intake tube is moved into the rinsing vessel by rotating the lever 42 and rotating the carrier 32. The rinsing liquid pump 50 is actuated and cleans the intake tube 38. After this washing process has been completed, the lever 42 is lifted again. Air is sucked in. The carrier 32 is rotated such that the additional liquid vessel 36 gets into the operative position. This liquid vessel contains a reagent, and the intake tube 38 dips into this liquid vessel 56. The sample pump takes in, for example, 10 microliters of reagent. The lever 42 moves the intake tube 38 into the graphite tube 14, and the sample pump 44 adds these 10 microliters of reagent together with 15 microliters of air to the sample already present in the graphite tube. Now the power unit 68 is switched on. The program of the graphite tube atomizer with drying, decomposing, atomizing and measuring is started in conventional manner. In the meantime, the arm 42 is moved back into the rinsing vessel. After the measuring cycle has been completed, the power unit 68 provides a signal which initiates a new sample feeding process.

Calibration measurements may precede the sample measurements. To this end, the turntable 18 and the carrier 32 are rotated in accordance with the program such that the respective desired liquid vessels with blank or calibration solution are moved into the operative position.

The control operation required therefor is effected in such a way that the desired positions of the carrier 32 and of the turntable 12 are provided in digital form. The carrier servomotor 36 and the turntable servomotor 28 are driven, until the carrier position sensor and the turntable position sensor provide the desired digital signals. The accurate adjustment of the turntable and of the carrier to the position required is then effected within the sector in which the digital position signals are provided by means of the dashed or arcuate marks 154 and 166, respectively, and of the dotted marks in the tracks 144 and 164, respectively. Instead of using a turntable code disc of transparent material having opaque markings, it is also possible to provide a turntable code disc of opaque material with transparent markings. This offers the advantage that the light barriers are exposed to less stray light.

We claim:

1. Sample feeding device for automatically feeding samples into a graphite tube atomizer provided with a sample inlet opening, comprising:
   a turntable adapted to accommodate a circular array of liquid vessels, said turntable including a turntable position sensor connected to said turntable, which sensor supplies a turntable position signal to a control device;
   a turntable servomotor for driving said turntable, said turntable being arranged to be rotated by said turntable servomotor into positions determined by the program of said control device only and monitored by said turntable position signal;
   a carrier, pivotably movable relative to an instrument base plate, is arranged to carry said turntable and said turntable servomotor, said carrier being arranged to be displaced by a separate carrier servomotor, said carrier having a carrier position sensor affixed thereto for applying a carrier position signal to said control device;

an intake tube movable between a first position and a second position by means of an intake tube servomotor, said intake tube, in its first position, dipping with one end into a respective liquid vessel located in an operative position, and, in its second position, extending with said one end into said sample inlet opening of said graphite tube atomizer;

a control device, adapted to control said intake tube servomotor, said turntable servomotor and said carrier servomotor in accordance with a certain program such that liquids from different liquid vessels are sucked into said intake tube and are discharged into said graphite tube atomizer and that in one position of said carrier said further liquid vessel is located below said intake tube when said intake tube is in its first position.

2. Sample feeding device as set forth in claim 1, characterized in that a rinsing liquid pump feeding in one direction only is connected to said other end of said intake tube and communicates with a rinsing liquid container, a rinsing vessel is arranged on said carrier radially outwardly of said turntable; and in one position of said carrier said rinsing vessel is located below said intake tube, when this tube is in its first position, the movement of said rinsing liquid pump and of said carrier servomotor being so coordinated by the program that between the individual sample feeding steps said rinsing liquid pump feeds rinsing liquid through said intake tube into a waste vessel.

3. Sample feeding device as set forth in claim 2 characterized in that said turntable position sensor comprises a code disc in the form of an annular disc connected to said turntable and having arcuate tracks with markings, which are arranged to be scanned by light barriers, the various angular positions of said turntable being digitally encoded by said markings.

4. Sample feeding device as set forth in claim 3, characterized in that a further track of said turntable code disc is arranged to be scanned by a light barrier and has dotted marks thereon, each of which defines one of said encoded positions of said turntable, in which a liquid vessel is in the operative position below said intake tube.

5. Sample feeding device as set forth in claim 4, characterized in that a further track of said turntable code disc is arranged to be scanned by a light barrier and has dashed or arcuate marks, which extend from the radius passing through a respective one of said dotted marks in circumferential direction to the radius which passes through the end of said marking associated with this dotted mark and encoding the respective position of said turntable, and when the position marking selected by the program has been reached, the direction of rotation of said turntable servomotor is arranged to be controlled depending on such an arcuate mark being detected or not such that the associated dotted mark is set on the light barrier responding thereto.

6. Sample feeding device as set forth in claim 1, characterized in that the carrier position sensor comprises a code disc of the transparent material which is connected to the carrier and has tracks with opaque markings thereon, which are arranged to be scanned by light barriers, the various positions of said carrier being digitally encoded by the markings.

7. Sample feeding device as set forth in claim 6, characterized in that four positions of said carrier are binarily encoded by two tracks, and said intake tube, in the first position, is located above the inner circular array of liquid vessels of said turntable, in the second position is located above the outer circular array of liquid vessels of said turntable, in the third position is located above the rinsing vessel, and in the fourth position is located above the further liquid vessel.

8. Sample feeding device as set forth in claim 7, characterized in that a further track of said carrier code disc is arranged to be scanned by a light barrier and has dotted marks thereon, each of which marks an exactly defined position of said carrier, which is designated by the code marking.

9. Sample feeding device as set forth in claim 8, characterized in that a further track of the carrier code disc is arranged to be scanned by a light barrier and has dashed or arcuate marks thereon, each of which extends from a spot adjacent a respective one of the dotted marks to the spot which is adjacent the end of the marking associated with this dotted mark and encoding the position of said carrier, and when the position marking selected by the program has been reached, the direction of rotation of said carrier servomotor is arranged to be controlled, depending on such an arcuate mark being detected or not, such that the associated dotted mark is set on the light barrier responding thereto.

* * * * *